United States Patent [19]
Hatch et al.

[11] Patent Number: 4,900,669
[45] Date of Patent: * Feb. 13, 1990

[54] DUAL-STAGE FERMENTATION

[75] Inventors: Randolph T. Hatch, Wellesley; Keith C. Backman, Bedford, both of Mass.

[73] Assignee: Biotechnica International, Inc., Cambridge, Mass.

[*] Notice: The portion of the term of this patent subsequent to Jun. 16, 2004 has been disclaimed.

[21] Appl. No.: 760,819

[22] Filed: Jul. 31, 1985

Related U.S. Application Data

[63] Continuation-in-part of Ser. No. 605,488, Apr. 30, 1984, Pat. No. 4,673,640.

[51] Int. Cl.⁴ .................. C12P 13/22; C12P 21/00; C12N 9/00; C12N 15/00
[52] U.S. Cl. .................................. 435/108; 435/3; 435/41; 435/69.1; 435/172.3; 435/183; 435/252.3; 435/320; 935/29; 935/43; 935/56; 935/73
[58] Field of Search ............. 435/3, 172.3, 108, 183; 935/41, 43, 60

[56] References Cited

U.S. PATENT DOCUMENTS

| | | | |
|---|---|---|---|
| 3,328,262 | 6/1967 | Lindblom et al. | 435/3 |
| 4,418,145 | 11/1983 | Weisrock et al. | 435/104 |
| 4,520,104 | 5/1985 | Heady et al. | 435/160 |
| 4,673,640 | 6/1987 | Backman | 435/68 |

OTHER PUBLICATIONS

Plasterk et al. *Virology* 127: 24–36 (1983), Apr. 18).
Echols et al. *In. Lambda II,* Cold Spring Harbor Laboratory Publishers, Hendrix et al. eds., 1983.

*Primary Examiner*—Thomas D. Mays

[57] ABSTRACT

A method of continuous product formation using at least two continuous fermentation units and a microorganism capable of being induced, in response to environmental conditions, to undergo a genetic alteration from a state favoring microorganism growth to a state favoring product production by the microorganism. The first continuous fermentation unit is maintained at environmental conditions selected to favor growth of the microorganism and to be nonpermissive for the genetic alteration. The microorganism is grown continuously in the first unit, and a portion of the growing microorganism cell mass is transferred via connecting means to the second continuous fermentation unit. Either the connecting means or the second unit is maintained at second environmental conditions selected to effect the genetic alteration. The altered microorganism is cultured in the second unit. Exudate from this second fermentor (containing microorganism mass and medium) is continually removed and the product which is present, either in the microorganisms themselves or the medium surrounding them, is extracted.

5 Claims, 1 Drawing Sheet

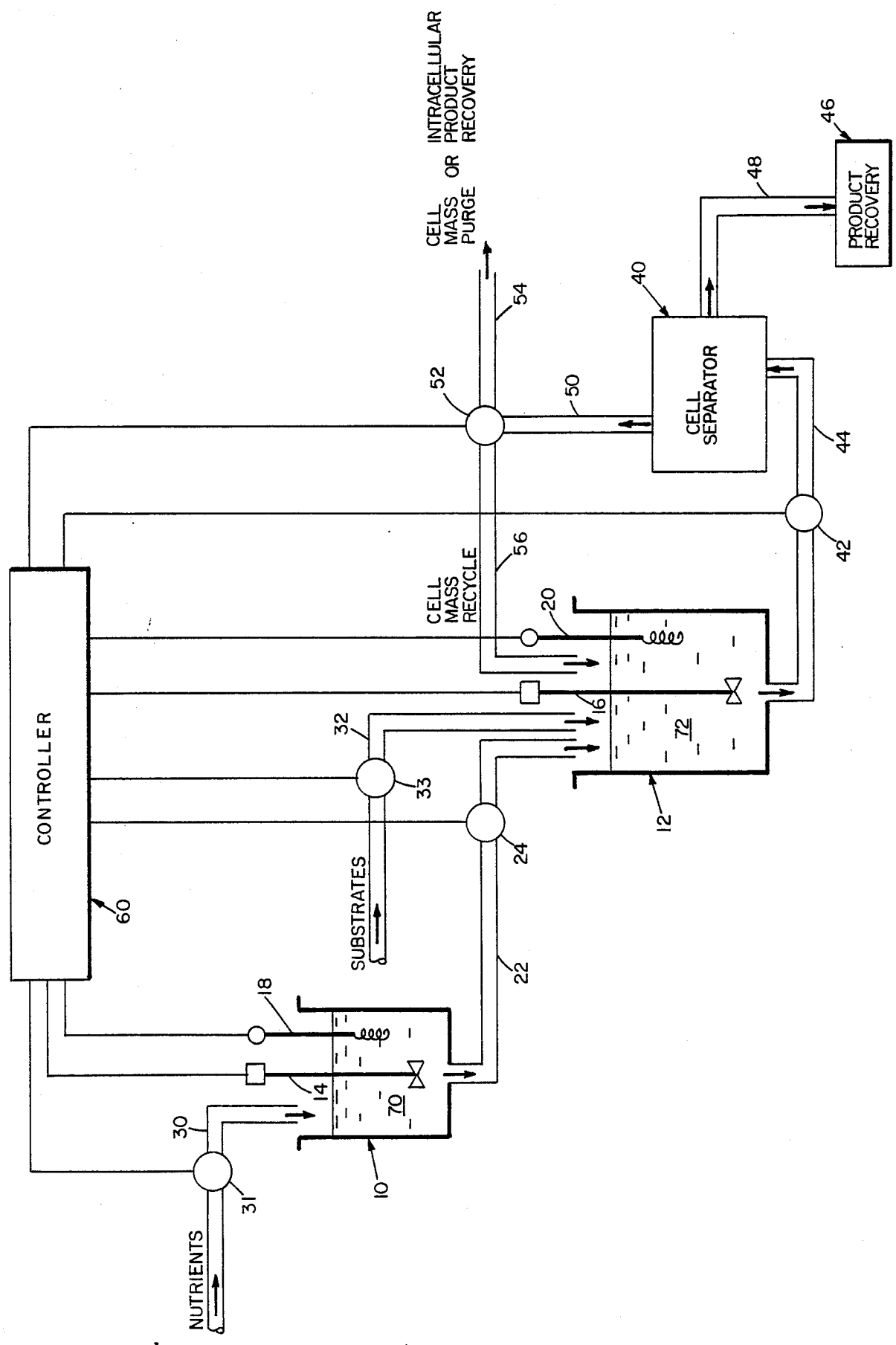

DUAL-STAGE FERMENTATION

This application is a continuation-in-part of Backman USSN 605,488 filed Apr. 30, 1984, now issued as U.S. Pat. No. 4,673,640.

BACKGROUND OF THE INVENTION

This invention relates to a method of multistage continuous fermentation.

Continuous fermentation of microorganisms involves the continual removal of broth and microorganisms from a fermentor coupled with the addition of fresh medium so that no change in volume, or other relevant parameters, occurs. The rate of removal and addition determines the rate at which the microorganisms may grow. Similarly, the medium and environmental conditions will determine the biochemical pathways which the microorganisms utilize, and therefore the end products of the fermentation.

Lindblom et al. U.S. Pat. No. 3,328,262, discloses apparatus having two continuous fermentation vessels comprising (a) a growth vessel for Xanthomonas with minimal product formation and (b) a production vessel for polysaccharide production. The vessels are controlled so that pH, temperature, oxygen and mean cell residence time are optimal for growth or product production, respectively.

Heady et al. U.S. Pat. No. 4,520,104 discloses the production of butanol by a continuous fermentation process using Clostridium acetobutylicum. The process involves the use of a continuous culture vessel containing cells in a logarithmic phase of growth, which provides a continuous inoculum for a second fermentation vessel. The butanol produced by these cells is detrimental to their growth and thus conditions in the first fermentor are maintained such that the level of butanol is minimal. Butanol formed in the second fermentation vessel is removed continuously using a filter system, and the cells are periodically recycled.

Weisrok et al. U.S. Pat. No. 4,418,145 discloses the production of Xanthomonas campestrius and a process for its use to produce xanthan from a nutrient medium. Either one or two fermentors may be used. If two fermentors are used, the first provides logarithmically growing cells to the second fermentation unit which contains a nutrient medium similar to that of the first unit but with more glucose to induce product formation. Xanthan is continually removed from the effluent of the second fermentor.

SUMMARY OF THE INVENTION

This invention features a method of continuous product formation using at least two continuous fermentation units and a microorganism capable of being induced, in response to environmental conditions, to undergo a genetic alteration from a state favoring microorganism growth to a state favoring product production by the microorganism. The first continuous fermentation unit is maintained at environmental conditions selected to favor growth of the microorganism and to be nonpermissive for the genetic alteration. The microorganism is grown continuously in the first unit, and a portion of the growing microorganism cell mass is transferred via connecting means to the second continuous fermentation unit. Either the connecting means or the second unit is maintained at second environmental conditions selected to effect the genetic alteration. By continuous fermentation unit, it is meant that components (e.g. nutrients, alkali or acid for PH control, product-forming substrate) are continuously added as necessary, and other components (e.g. microorganism cell mass and medium) are removed continuously as necessary. The altered microorganism is cultured in the second unit. Exudate from this second fermentor (containing microorganism mass and medium) is continually removed and the product which is present, either in the microorganisms themselves or the medium surrounding them, is extracted.

In the preferred embodiment the two environments within the continuous fermentation units differ in their temperature of operation. The growth fermentor is maintained at a temperature that is nonpermissive for the genetic alteration, whereas the second fermentor is maintained at a temperature permissive for such alteration. The alteration is effected in response to the activation or inactivation of a temperature-sensitive phage lambda repressor and the temperatures are selected to maintain and to inactivate that repressor activity, respectively. Specifically, the temperatures are below 40° C. and above 40° C., respectively. The genetic alteration preferably is a recombination process (e.g. site-specific recombination) such as one in which two inactive DNA segments are juxtaposed to create an actively expressed gene.

Other features and advantages of the invention will be apparent from the following description of the preferred embodiment and from the claims.

DESCRIPTION OF THE PREFERRED EMBODIMENT

The drawing will first briefly be described.

DRAWINGS

The FIGURE is a diagrammatic representation of the fermentation apparatus.

Cells

Microorganisms that can be used in this process are those in which the production of a product, or the conditions required to form the product, harms the cell in some way, for example, by slowing its growth rate or killing it. If such a cell can be grown under conditions in which product production is inhibited, but subsequently can be induced to make product, then this process will enhance production of the product. Specifically, the cells are genetically engineered so that they will undergo a genetic alteration that changes them from a growth-favoring state to a product-production favoring state. The genetic alteration is readily effected by controlling a physical characteristic of the cell environment.

Apparatus

Referring to the FIGURE, cell growth fermentation tank 10 and product formation fermentation tank 12 are provided respectively with mechanical agitators 14 and 16 and with independently thermostatically controlled heating/cooling coils 18 and 20. Transfer pipe 22, with valve and/or pump 24, connects the bottom of tank 10 to the top of tank 12 for transfer of fermentation medium (including cells) from tank 10 to tank 12. Feed pipes 30 and 32 (with respective valves 31 and 33) are provided for introduction of cell growth nutrient into tank 10 and product formation substrates into tank 12, respectively. Cell separator 40 (such as a filter or centrifuge) has its input connected to outlet pipe 44 via pump 42 from the bottom of tank 12. Cell separator 40 has one output (for extracellular product and/or spent nutrients) to product recovery element 46 via pipe 48. Cell separator 40 has a second output (for cell mass and intercellular product) connected via pipe 50 to valve and/or pump 52 for cell mass purge (or for cell-mass and product recovery, where the product is intracellular) through pipe 54 and cell mass recycle to tank 12 through pipe 56. Controller 60 regulates valves 24, 31, 33 and 52, pump 42, heating/cooling coils 18 and 20, and mechanical agitators 14 and 16. For aerobic fermentations (e.g. as in Examples 1-3), the appropriate gas feed lines are added to the bottom of both fermentation tanks 10 and 12.

Process

In general, cell growth fermentation tank 10 is continuously filled with medium 70 consisting of nutrients optimum for the growth of microorganisms without product formation, but such that the cells will be in a condition suitable to allow induction of product formation. Optimal environmental conditions are maintained and controlled by controller 60 which controls using mechanical agitator 14 and heating/cooling element 18 as well as the various pumps and valves of the apparatus. As the microorganisms grow, they are continuously transferred through valve 24 in pipe 22 to the product production tank 12. The environmental conditions in this production tank are controlled and maintained by controller 60 using mechanical agitator 16 and heating-/cooling unit 20. Substrate required for product formation is added through pipe 32 (with valve 33). Conditions in this tank are maintained so that they effect a genetic alteration that favors product formation over cell growth. Once these alteration-effecting conditions are established, and the cells have been cultured to a desired population for product production, some of the medium 72 containing unused substrates and nutrients, microorganisms and the desired product is removed through pipe 44 (with pump 42) to cell separator 40, so that the microorganisms (or cell mass) may be separated from the rest of the medium, to give a broth which is removed via pipe 48 to a product or spent medium recovery unit 46. This unit functions to concentrate and purify the desired product or dispose of the spent cell free broth. The cell mass from the cell separator 40 is passed through pipe 50 (with valve 52) to be either recycled to the product production tank 12 using pipe 56 and/or to be removed using pipe 54. If the product is primarily intracellular, it will be recovered from the cell mass by lysing the cells using standard procedures (see example 2, below). If the product is extracellular, it can be recovered from the medium by suitable recovery techniques. Suitable such procedures, e.g., for the product phenylalanine, are disclosed in Hatch USSN 706,041, filed Feb. 27, 1985, which is hereby incorporated by reference.

Once optimized, the process can be maintained in a continuous fashion so that nutrients and substrates are continually being added to tanks 10 and 12, and media 70 and 72 are being continually removed. This results in a continuous formation of the desired product.

EXAMPLE 1

Cells including an excisable chromosomal element, such as those described in Backman et al. U.S. Application USSN 701,091 (filed Feb. 13, 1985, and hereby incorporated by reference) are suitable for the process. In general, the excisable element in these cells contain an essential gene which can be excised in response to an external stimulus such as a rise in temperature. When this gene is excised the cells can no longer grow but they can synthesize a desired product. An example of such a cell is $E.$ $coli$ KB224::xKB803/pKB712 which can be grown in fermentor 10 at 30° C. in M9 medium in a log Phase of growth (for example, to a cell density of 1-40 grams dry weight/liter) and fed into product fermentor 12, containing the same medium which is maintained at 42° C. The mean residence time of cells in fermentor 12 is 2-20 hours and the product (in this example, phenylalanine) is excreted into the medium 72 and recovered in unit 46. Examples include the excision of genes for the biosynthetic pathways of tyrosine, tryptophan, threonine, isoleucine or proline such as tyrA, tyrR, trpE, tna, trpR, aroP, pheA, ppc and the gene encoding proline-oxidase.

EXAMPLE 2

Cells such as those described in Backman U.S. Application USSN 605,488 (filed Apr. 30, 1984, and hereby incorporated by reference) U.S. Pat. No. 4,673,640, are suitable for the process. In general, these cells contain genetic material which can be activated to undergo rearrangement by a recombination process which in one embodiment is triggered by a rise in temperature. The rearrangement either can activate a product-formation enhancing gene or it can inactivate a growth-enhancing gene. One such cell is $E.$ $coli$ KB204/pKB730 which be utilized, in much the same way is the cells in Example 1 above, by growing in fermentor 10 at 30° C. in M9 medium at a cell density of 1 to 40 grams dry weight/liter. Product fermentor 12 also contains M9 medium but is maintained at 42° C. The mean residence time in this fermentor is 0.5-3 hours and the product (in this case, T4 ligase) is produced intracellularly and recovered by lysing the cells and eluting the lysate on a phosphocellulose column as described in USSN 605,488, cited above.

EXAMPLE 3

Cells such as those described in Backman U.S. Application USSN 655,361 (filed Sept. 27, 1984, and hereby incorporated by reference) are also suitable for this process. In general, these cells contain a chromosomally located episomal element comprising a gene favoring product production. The episomal element can be induced to form a plasmid which replicates to high copy number and thus favors production of the desired product. An example of such a cell is $E.$ $coli$ transformed with eKB101 that has been modified by including a gene coding for a desired product. Similarly to Examples 1 and 2, the transformed $E.$ $coli$ is grown in fermentor 10 at 30° C. in M9 medium at a cell density of 1 to 40 grams dry weight per liter and transferred to fermentor 12 which is maintained at 42° C. and purified by a process selected according to the product being produced.

OTHER EMBODIMENTS

Where the genetic rearrangement between a growth mode and a product-production mode is reversible, the cells from the production fermentor may be fed back to the growth fermentor, as necessary. The integration, rather than excision, of an autonomously replicating element can also yield an active product-producing integrated element, as can the integration of just a part of a gene. For example, a promoter-containing fragment could be inserted in front of a promotorless product-producing gene to activate it; or a gene fragment can be inserted into a repressor gene to inactivate it, and thereby activate a normally repressed product-producing gene. Similarly, genetic recombination can give rise to a nonfunctional gene from a previously functional growth-favoring gene. The fermentation vessels can be gas agitated, in lieu of mechanical agitation. The genetic alteration can be effected by heating the means connecting the two fermentors, or by including another fermentor between the two fermentors, which is maintained at a temperature to induce the genetic alteration. In the latter case, if the alteration is irreversible or can be prevented by selection pressure, the product-producing fermentor can be maintained at conditions that optimize product production without regard to inducing the alteration.

We claim:

1. A method for continuously fermenting bacterial cells to form a product, said method comprising:
   (a) providing at least a first and a second continuous fermentation unit and a means connected between said units to communicate therebetween;
   (b) providing a strain of recombinant bacterial cells capable of being induced to undergo genetic rearrangement from a first genetic configuration to a second genetic configuration, said genetic rearrangement being lambdoid bacteriophage site-specific recombination mediated by lambdoid bacteriophage xis and int genes in response to an environmental shift from a first environmental condition, which is non-permissive for said genetic rearrangement, to a second environmental condition, which permits genetic rearrangement to form said second genetic configuration, said genetic rearrangement juxtaposing two inactive DNA segments to create an actively-expressed gene encoding a protein or polypeptide which is said product, or an intermediate or enzyme in a synthetic pathway of said product, said two inactive DNA segments being heterologous with respect to said lambdoid bacteriophage xis and int genes;
   (c) continuously growing said bacterial cells in said first fermentation unit under said first environmental condition to establish a microorganism mass;
   (d) transferring at least a portion of said microorganism mass from said first continuous fermentation unit through said means connecting said units to said second continuous fermentation unit;
   (e) continuously culturing said bacterial cells in said second fermentation unit under production-favoring conditions, said second fermentation unit being maintained at said second environmental condition, whereby said bacterial strain in said second unit is subject to said genetic rearrangement effecting expression of said actively-expressed gene and production of said desired product in said second unit;
   (f) removing an exudate of said microorganism mass from said second unit and removing said product from said exudate; and
   (g) recycling at least a portion of the cell mass of said exudate of step (f) into said second unit, said portion being sufficient to maintain a desired cell density in said second unit.

2. The method of claim 1 in which said environmental shift is a shift in temperature, said first environmental condition being a first temperature and said second environmental condition being a second temperature.

3. The method of claim 2 in which said first temperature is below 37° C.

4. The method of claim 1 in which said genetic rearrangement is induced responsive to a phage lambda repressor, one of said environmental conditions being selected to provide repressor and the other of said environmental conditions being non-permissive for active repressor.

5. The method of claim 1 in which said cells are members of species *Escherichia coli*.

* * * * *